United States Patent
Zimmermann et al.

(10) Patent No.: US 10,393,653 B2
(45) Date of Patent: Aug. 27, 2019

(54) METHOD AND DEVICE FOR OPTICALLY DETECTING A MOVEMENT IN A BIOLOGICAL SAMPLE

(71) Applicant: Fraunhofer-Gesellschaft zur Foerderung der angewandten Forschung e. V., Munich (DE)

(72) Inventors: Heiko Zimmermann, Waldbrunn (DE); Frank Stracke, Saarbruecken (DE); Ronan Le Harzic, Woustviller (FR)

(73) Assignee: Fraunhofer-Gesellschaft zur Foerderung der angewandten Forschung e. V., Munich (DE)

( * ) Notice: Subject to any disclaimer, the term of this patent is extended or adjusted under 35 U.S.C. 154(b) by 0 days.

(21) Appl. No.: 15/770,356

(22) PCT Filed: Oct. 26, 2015

(86) PCT No.: PCT/EP2015/002122
§ 371 (c)(1),
(2) Date: Apr. 23, 2018

(87) PCT Pub. No.: WO2017/071721
PCT Pub. Date: May 4, 2017

(65) Prior Publication Data
US 2018/0321219 A1 Nov. 8, 2018

(51) Int. Cl.
*G01N 21/49* (2006.01)
*G01N 21/47* (2006.01)
(Continued)

(52) U.S. Cl.
CPC ......... *G01N 21/4788* (2013.01); *G01N 21/21* (2013.01); *G01N 21/49* (2013.01); *G01N 2021/479* (2013.01); *G01P 13/00* (2013.01)

(58) Field of Classification Search
CPC .......... G01N 33/5005; G01N 2021/479; B01L 3/502; G01H 9/00; H04N 5/144
See application file for complete search history.

(56) References Cited

U.S. PATENT DOCUMENTS 5,535,302 A * 7/1996 Tsao ..................... G06K 9/4619
706/20
6,549,801 B1 * 4/2003 Chen .................... A61B 5/0073
250/350

(Continued)

FOREIGN PATENT DOCUMENTS

EP 2342317 B1 12/2012
EP 2955505 A1 12/2015
(Continued)

OTHER PUBLICATIONS

Sridhar Rao, https://www.youtube.com/watch?v=ujzSmsmg7ok, 2010.*
(Continued)

*Primary Examiner* — Maurice C Smith
(74) *Attorney, Agent, or Firm* — Caesar Rivise, PC

(57) ABSTRACT

The invention relates to a method and a device for the optical in vitro detection of a movement in a biological sample and/or for the optical in vitro detection of a movement of a component of the biological sample. The method has the following step: (a) providing an optical wide-field illumination device for illuminating the sample, said device being designed to illuminate the entire sample, and a detector (3) for detecting radiation (9; 9a, 9b) coming from the sample. The detector (3) has a detection surface (3a) which is divided into multiple detection regions (4a). The detector is additionally designed to derive (S1) detection signals (4c) of individual detection regions (4a) with respect to time, subsequently rectify (S2) the signals, preferably by generating an absolute value or squaring, and summing or averaging (S3) the derived and rectified detection signals of all of the (Continued)

detection regions and then providing same as an output signal (6c). The method further has the steps of illuminating the sample using the wide-field illumination device and detecting a movement in the biological sample on the basis of the output signal (6c) of the detector (3).

19 Claims, 5 Drawing Sheets

(51) Int. Cl.
*G01P 13/00* (2006.01)
*G01N 21/21* (2006.01)

(56) References Cited

U.S. PATENT DOCUMENTS

| | | | | |
|---|---|---|---|---|
| 7,582,415 | B2* | 9/2009 | Straus | B82Y 20/00 435/4 |
| 7,864,338 | B2* | 1/2011 | Pouet | G01B 9/02045 356/502 |
| 2006/0055772 | A1* | 3/2006 | Rosen | G02B 27/48 348/31 |
| 2014/0036272 | A1* | 2/2014 | Nadkarni | G01N 21/4795 356/450 |
| 2015/0369790 | A1 | 12/2015 | Iwai et al. | |

FOREIGN PATENT DOCUMENTS

| | | |
|---|---|---|
| WO | 2012112977 A1 | 8/2012 |
| WO | 2014123156 A1 | 8/2014 |

OTHER PUBLICATIONS

Ansari et al. (2016). Real time monitoring of drug action on T. cruzi parasites using a biospeckle laser method. Laser Physics, 26, 065603: 1-4.

Ansari et al. (2016). Online fast biospeckle monitoring of drug action in trypanosoma cruzi parasites by motion history image. Lasers Med Sci, 31, 1447-1454.

Brunel et al. (2017). Structure and dynamics of multicellular assemblies measured by coherent light scattering. New Journal of Physics, 19, 073033: 1-12.

Cole et al. (1996). Laser speckle spectroscopy—a new method for using small swimming organisms as biomonitors. Bioimaging, 4(4), 243-253.

Pomarico et al. (2004). Compact device for assessment of microorganism motility. Review of Scientific Instruments, 75(11), 4727-4731.

International Search Report from corresponding PCT/EP2015/002122 dated Jul. 21, 2016.

* cited by examiner

20

METHOD AND DEVICE FOR OPTICALLY DETECTING A MOVEMENT IN A BIOLOGICAL SAMPLE

CROSS-REFERENCE TO RELATED APPLICATIONS

This application is a U.S. National Phase Application of PCT/EP2015/002122, filed Oct. 26, 2015, the contents of which application are incorporated herein by reference in their entireties for all purposes.

The invention relates to a method and a device for optical in vitro detection of a movement in a biological sample and/or for optical in vitro detection of a movement of a component of the biological sample, wherein the diameter of the biological sample is preferably at least 100 µm.

It is known from practice in the art that a need exists for monitoring the active dynamic of closed and three-dimensional cell and tissue cultures in fields such as developmental biology, toxicity tests and pharmaceutical research.

For example, tissue fragments cultured from embryonic stem cells, which have differentiated to a muscle tissue are used in the context of toxicity tests in order to test the toxicity of a substance being tested. Herein, it is investigated whether a substance applied to the muscle tissue influences the contractions of the muscle tissue, which can be an indicator for the toxicity of the substance. For this purpose, measuring methods are required to detect a movement, for example a contraction, in such a three-dimensional biological sample in the form of a cluster of cells. Typical diameters of such cell clusters are 50 to 400 µm, although diameters in the millimeter range are also possible.

These studies are currently carried out primarily by visual observation and seldom by video microscopy with subsequent image analysis. The former are time-consuming and always associated with subjective estimates. The latter has the disadvantage that complex imaging optical systems and a complex image analysis, associated with a significant computational effort, are required. A further disadvantage is its inherent sensitivity to slight displacements.

Non-optical methods such as impedance measurements function only in contact with the sample. If, however, the sample form deviates from a plane (adherent monolayer) or is three-dimensional, or even freely floating in a medium, the aforementioned techniques are not usable.

Automated imaging methods have the disadvantage that, for example, with a depth of field of, for example 10 µm and the aforementioned typical size of a cell cluster of 50 to 400 µm, 5 to 40 image planes have to be covered in the sample. In a typical minimum measurement duration of approximately 10 seconds to be able to detect a movement and the additional time needed for re-positioning and/or focusing, such methods are not suitable for monitoring a large number of samples rapidly.

A serial measurement of large numbers of samples is generally not called for due to the very long observation duration because of the time scales of biological dynamics. In practice, however, there is a need to carry out such movement detection on a large number of separate samples held for example, in a multiwell plate, also known as a microtiter plate, for example, with samples held in 96 or 384 cavities (also "wells"). Imaging methods are not suitable for a parallel measurement of a plurality of such samples since for geometric and structural space reasons, a conventional imaging optical device arranged at each cavity of a multiwell plate is difficult to realize.

It is therefore an object of the invention to provide an improved method for detecting a movement in a biological sample and/or a movement of a sample component of the biological sample, with which disadvantages of conventional techniques can be avoided. It is, in particular, an object of the invention to provide a robust, contact-free method for movement detection that does not require complex image analysis. It is a further object of the invention to provide a method which is suitable for the parallel analysis of a plurality of samples in a screening environment. It is a further object to provide a device for detecting a movement in a biological sample with a spatial extent, with which the disadvantages of conventional devices can be avoided.

These objects are achieved with devices and methods of the invention, which are disclosed in greater detail in the following description, making partial reference to the drawings.

According to a first aspect of the invention, a method is provided for optical in vitro detection of a movement in a biological sample and/or a movement of a component of the biological sample. The biological sample is a biological sample with a spatial extent. The biological sample is preferably a biological sample which comprises a plurality, in particular a large number, of biological cells. The diameter of the biological sample can be at least 50 micrometers (µm) in at least one spatial direction, preferably in all spatial directions and is often more than 100 µm in all spatial directions. A further variant provides that a diameter of the biological sample is greater than a refraction-limited resolution achievable by the optical wide-field illumination apparatus. However, the invention is not restricted to biological samples with such dimensions.

The biological sample can be a three-dimensional cell and/or tissue culture, for example, in the form of a cell cluster. The biological sample can comprise, in particular, living cells, for example, muscle cells or generally cells which have an active dynamic capability and/or can initiate a movement. Detection of a movement in the biological sample should be understood, in particular, to mean a movement within the sample or a movement of a component of the biological sample. In other words, it should be possible to detect in general dynamic phenomena in or within biological samples with a spatial extent. In cell cultures of muscle cells, such movements can be initiated, for example, by contraction of individual muscle cells.

The biological sample, however, can be a sample of free-swimming microorganisms, for example, spermatozoa. In this case, the method for detecting the movement of the free-swimming microorganisms can be used, for example in the case of spermatozoa, for determining sperm motility.

The biological sample is also denoted below, for short, as the sample. Preferably, the diameter of the sample is not more than 5 mm, further preferably not more than 1 mm.

The inventive method comprises the provision of an optical wide-field illumination apparatus for illuminating the sample, which is configured to illuminate the whole sample and furthermore the provision of a detector for detecting the radiation coming from the sample.

The detector has a detection area that is subdivided into a plurality of detection regions. For example, the detector can be a two-dimensional pixel array detector with pixel elements arranged matrix-like, e.g. an optical pixel sensor. According to one variant of the invention, the detection area can be subdivided into at least 10×10 or at least 100 detection regions. The detection area of the detector can be subdivided into, for example, 10,000 or more detection regions, e.g. pixels, arranged in multiple rows adjoining one another, for example, in 100×100 or more pixels or channels. The greater the spatial resolution or the pixel count, the more reliably it can be ensured that movement-induced changes in the detected intensity do not average out, but can be cumulatively detected.

The device, in particular the detector, is configured to form the derivative with respect to time of detection signals of individual detection regions, subsequently to rectify them, the rectification preferably taking place by absolute value generation or squaring, and to sum or to average the differentiated or rectified detection signals of all the detection regions. Forming the derivative of detection signals of individual detection regions with respect to time means that in each case the nth derivative, $n>=1$, with respect to time of the detection signal of each detection region, for example each pixel, is determined. Preferably, the first time derivative is determined in each case, i.e. $n=1$.

According to the invention, therefore, a detector with a spatially resolving detection area in the form of the individual detection regions, which are hereinafter also designated channels or pixels, is used. The measurement signals or measurement curves of the individual detection regions can be present in digital or analogue form and, in a first step, undergo differentiation with respect to time and are then rectified. Subsequently, however, the rectified signals or data of the individual detection regions are summed or averaged and thus result in a quantitative measure of the dynamics in a pattern or image generated by the sample on the detection area. Externally, the area-cumulative movement sensor therefore appears as a detector which outputs a non-spatially resolved signal or non-spatially resolved data. The detector can therefore be configured so that it outputs a single-channel signal. Complex analysis such as pattern recognition and trajectory formation in order to measure and define dynamic parameters are dispensed with.

The detector is thus preferably a non-image forming detector. The output signal of the detector can be analogue or digital.

A further advantage lies therein that dynamic phenomena in the sample are recognized through brightness changes or intensity changes on the detection area in that with the inventive measuring approach, the total or the average of the quantitative brightness changes which, with a constant illumination strength, are generated by dynamic phenomena in the sample, are measured cumulatively over the area, i.e. over the whole detection area. This prevents individual positive or negative measurements cancelling one another out. Furthermore, the sensitivity of the measurement is increased.

An optical wide-field illumination apparatus should be understood as a non-scanning illumination apparatus, i.e. an illumination apparatus by means of which the whole sample can be illuminated without the use of an optical system for focusing on individual image planes within the sample or without the use of an optical system for successively scanning the sample volume. In such a wide-field illumination apparatus, all the signal contributions from the entire sample volume are detected simultaneously by the detector.

A further advantage of the inventive method is therefore that the method can be carried out using relatively simple optical elements, and optical systems for successively scanning the sample volume can be dispensed with. Therefore, the device for carrying out the method can be configured economical and structurally compact. The method also has only a slight susceptibility to errors from maladjustment.

Due to the simple evaluating capability and high sensitivity of the measurement signal and of the structurally compact design, the method is particularly suited to parallel monitoring of a plurality of samples and can be integrated for high process efficiency into screening environments or into automated high turnover processes, e.g. high-throughput screening processes.

According to a preferred embodiment, the formation of the derivative with respect to time and the subsequent rectification of the detection signals of individual detection regions is carried out by means of an integrated circuit. The integrated circuit can be, for example, a CMOS (complementary metal oxide semiconductor) circuit. This enables rapid processing of the measurement signals and an economical and structurally compact embodiment of the detector.

A movement in the sample and/or a movement of a sample component can be detected, for example, if a value of the output signal of the detector exceeds a pre-determined threshold value. In the case of muscle cells, a movement in the sample can also be detected if the output signal has a periodicity.

According to a particularly preferred embodiment, a movement in the sample is recognized on the basis of a change in the diffraction pattern. According to this embodiment, the optical wide-field illumination apparatus comprises a light beam source which generates coherent light, wherein at least a part of a diffraction pattern that is generated by light of the light beam source diffracted by the sample falls on the detection area.

In a diffraction pattern, each point of a pattern contains signal contributions from the whole sample. It is therefore sufficient in principle to detect with the detector a subregion of the diffraction pattern generated by the sample. A movement within the sample generates a change in the movement pattern, for example a speckle pattern, although the overall brightness of the changing movement pattern remains approximately constant over time. Through the inventive measuring approach of subdividing the detection area into smaller detection regions and of rectifying the temporal change in the measurement curves before said curves are added or averaged, it is prevented that the changes generated by the movement in the sample become averaged out.

Particularly advantageous is a variant in which the whole diffraction pattern is imaged on the detection area. By this means, the sensitivity of the movement recognition is increased. In addition, the use of the whole pattern leads to a radically improved reproducibility of the measurements (as compared with the measurement of a small pattern portion) and to a certain quantitative comparability between similar samples.

Aside from the embodiment emphasized by way of example in which a movement in the sample is recognized due to a change in the diffraction pattern generated, the wide-field illumination apparatus can also be configured to reproduce an image of the sample on the detection area. According to this alternative embodiment, the optical wide-field illumination apparatus comprises a light beam source which can generate coherent or non-coherent light, and an optical system which is configured to generate an imaging optical path in order to image the sample on the detection area of the detector.

Here, widely differing wide-field illumination and/or imaging approaches can be used. For example, the optical wide-field illumination apparatus can be a transmitted-light microscope, a dark-field microscope or a wide-field fluorescence microscope. Depending on the type of wide-field illumination apparatus and/or the positioning of the detector relative to the sample, the radiation coming from the sample and detected by the detector can be radiation, in particular light, of a radiation source of the wide-field illumination apparatus which is altered at any desired position within the sample by an interaction with the sample in its radiation direction and/or its polarization state. This may concern transmitted light or fluorescence radiation.

The wide-field illumination apparatus can comprise an illumination optical system arranged on the illumination side, by means of which the radiation of the light beam source is directed to the entire sample in order to illuminate the sample completely and as evenly as possible. The optical system can also comprise a detection optical system by means of which the light emitted by the sample which through an interaction with the sample is changed in its beam direction, its polarization state and/or its diffraction pattern, is guided to a detection area of the detector. These functional properties of the illumination optical system and/or of the detection optical system can be realized by using one or more suitably arranged and configured known optical elements and components, for example, filters, lenses, apertures, refractive elements, etc.

The method can also comprise the provision of a receptacle for the sample. The receptacle for holding the sample can be a support matrix, preferably comprising a biopolymer. Furthermore, the receptacle can be configured as a support matrix situated in a hanging drop, preferably a biopolymer, such as for example, alginate. For the use of the method in screening environments, the receptacle for the sample can be a cavity of a multiwell plate (microtiter plate). Furthermore, the receptacle can be a cavity of a multiwell plate which is configured for forming a hanging drop on the individual cavities (a "hanging drop multiwell plate"). Such hanging drop multiwell plates are offered, for example, by the firm of Insphero AG of 8952 Schlieren, Switzerland under the designation "GravityPLUS™ 3D Culture and Assay Platform". EP 2 342 317 B1 discloses a plate of this type.

It has already been mentioned above that the method is particularly suitable for parallel monitoring of a plurality of samples, e.g. of samples which are to be examined in the context of automated high throughput methods. An advantageous development of the method therefore provides that therewith, a parallel optical detection of movements in a plurality of mutually separate biological samples or of movements of sample components in a plurality of mutually separate biological samples is carried out. According to this variant, the receptacle for the samples can be a multiwell plate or a hanging drop multiwell plate which has a plurality of cavities arranged in rows and columns to receive the samples. Furthermore, a plurality of detectors as described in this document are provided in the form of a detector arrangement, each detector of the detector arrangement being assigned to a cavity. Herein, a grid spacing of the individual detectors corresponds to a grid spacing of the cavities of the multiwell plate.

The diameter of the detection area of the detector can be smaller than or equal to 9 mm. This is particularly advantageous if the detector is used for movement detection of samples held in multiwell plates, in particular in 96 well plates.

With a parallel optical detection of a movement in a plurality of mutually separate biological samples which are each held in a cavity or a hanging drop of a multiwell plate, the optical wide-field illumination apparatus can be configured to illuminate the individual cavities. If coherent light is needed, for example, for the embodiment in which a diffraction pattern is detected, the optical wide-field illumination apparatus can be configured as a laser diode array, a grid spacing of the individual laser diodes corresponding to the grid spacing of the cavities of the multiwell plate. A laser diode array represents a space-saving and energy-efficient illumination source.

In place of a laser diode array as the light beam source, the light beam source can be configured as a conventional light source (laser, arc lamp, etc.), wherein the light of the light beam source is coupled into the individual cavities with contain the samples to illuminate the samples via an optical fiber bundle. Each optical fiber is allocated to a cavity. This offers the advantage that the light source can be operated sufficiently spaced from the sample in order to avoid excessive heat generation in the proximity of the sample.

Furthermore, according to a further alternative variant, there exists the possibility of illuminating the multiwell plate areally with a light beam source which represents a simple implementation variant, but has energy-efficiency disadvantages since the light beam source must have a corresponding power rating. It is advantageous if the light is parallelized via a suitably designed condenser lens and possibly angle-dependent pass filters and is fed in a targeted manner onto the cavities.

According to a second aspect of the invention, a device is provided for contact-free in vitro detection of a movement in a biological sample and/or a movement of a component of the biological sample. The diameter of the biological sample can be, for example, at least 50 µm. The device comprises an optical wide-field illumination apparatus for illuminating the sample, which is configured to illuminate the whole sample. The device further comprises a detector for detecting radiation coming from the sample, wherein the detector has a detection area that is subdivided into a plurality of detection regions. The detector is configured to form the derivative with respect to time of detection signals of individual detection regions, subsequently to rectify them, preferably by absolute value generation or squaring, and to sum or to average the differentiated and rectified detection signals of all the detection regions and then to provide them as an output signal.

According to a preferred embodiment of the invention, the detector has an integrated circuit, preferably a CMOS circuit which is configured to carry out the formation of the derivative with respect to time and the subsequent rectification of the detection signals of individual detection regions.

The detector can output a single-channel signal and/or a signal that is not spatially resolved with respect to the detection area.

According to a third aspect of the invention, a detector is provided for detecting optical radiation, having a detection area which is subdivided into a plurality of detection regions (4a), wherein the detector is configured to form the derivative with respect to time of detection signals of individual detection regions, subsequently to rectify them, preferably by absolute value generation or squaring, and to sum or to average the differentiated and rectified detection signals of all the detection regions and then to provide them as an output signal.

For the avoidance of repetition, features disclosed purely in the context of the device should also apply and be claimable as being disclosed in the context of the method and vice versa. The aforementioned aspects and inventive features, in particular with regard to the configuration of the detector or the optical wide-field illumination apparatus which have been described in relation to the method, therefore also apply, for example, for the device.

The preferred embodiments and features of the invention described above are combinable with one another as desired. Further details and advantages of the invention will now be described making reference to the accompanying drawings, in which:

The same components are provided with the same reference numerals in the figures and will not be described separately.

FIG. 1 shows a schematic representation of a method and a device according to one embodiment of the invention.

In order to carry out the method, a device is provided for optical in vitro detection of a movement in a biological sample 1. The biological sample 1 can be a cell cluster from muscle tissue.

The device comprises a receptacle (not shown) for the sample 1, an optical wide-field illumination apparatus 2 and a detector 3.

The receptacle is not restricted to a particular type of receptacle, but depending on the purpose and the type of sample, can suitably be configured, for example, as a carrier, a carrier plate, or a vessel, as a cavity of a multiwell plate or as a carrier matrix in the form of a biopolymer, e.g. an alginate, on which the sample is cultured.

Figure 1:
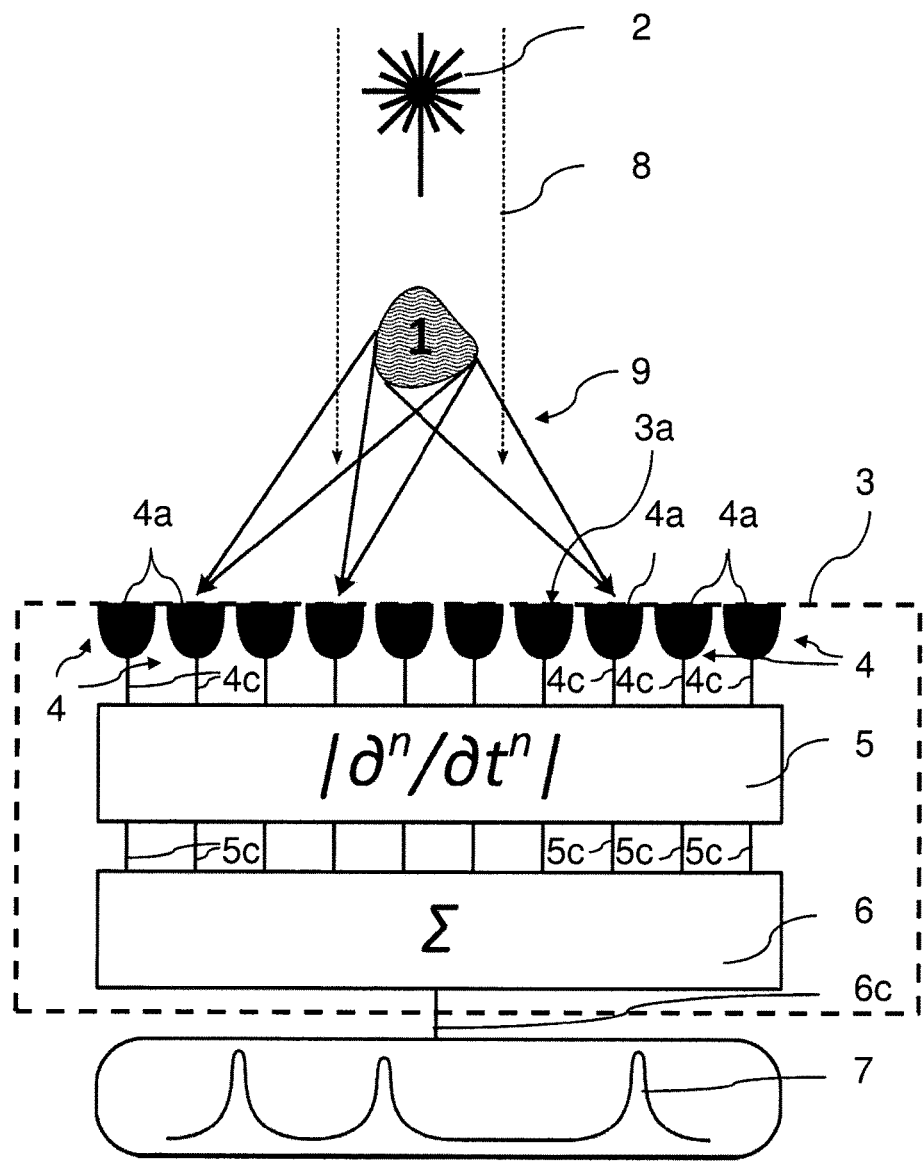
FIG. 1 shows a schematic representation of a method and a device according to an exemplary embodiment of the invention.

In the exemplary embodiment shown in FIG. 1, the optical wide-field illumination apparatus is a radiation source which generates coherent light (a laser). The whole sample 1 is illuminated by means of the coherent radiation 8 generated by the radiation source 2. For this purpose, it can be suitable to provide an illumination optical system (not shown), by means of which the radiation of the light beam source 2 is directed to the entire sample 1 in order to illuminate the sample completely and as evenly as possible. This functional property of the optical system can be realized by using one or more suitably arranged and configured known optical elements and components, for example, filters, lenses, apertures, refractive elements, etc.

Figure 2:
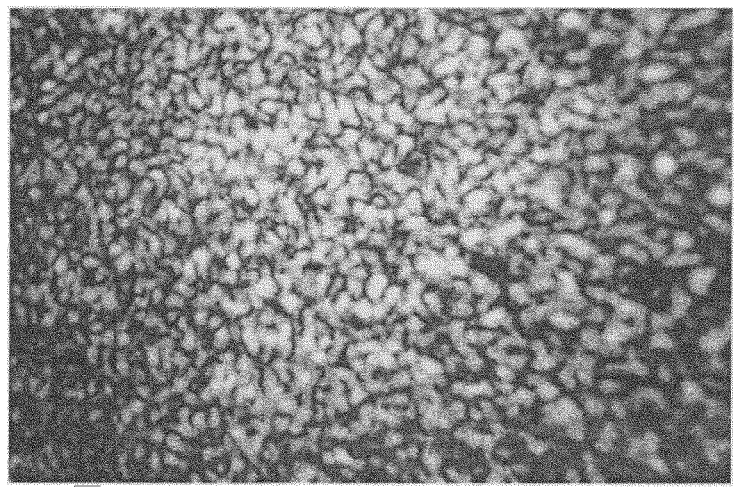
FIG. 2 shows a representation of a speckle pattern on the detector area.

The light of the light beam source 2 diffracted at the sample 1 creates a diffraction pattern with a center of high intensity and an edge region of low intensity in the form, for example, of a speckle pattern 20 which is shown, by way of example, in FIG. 2.

The device further comprises an optical detector 3 for detecting the diffraction pattern 20. The detector 3 is arranged so that the diffraction pattern 20 that is generated by the light 9 from the light beam source 2 diffracted by the sample 1 is imaged on the detection area 3a of the detector 3.

Herein, the detection area is formed as a two-dimensional pixel array area, so that the detection area 3a is subdivided by the individual pixels 4 into a plurality of detection regions 4a. The detection area is subdivided into a plurality of pixels 4, for example, into 10×10 or more pixels 4, which is not shown in the schematic diagram in FIG. 1. Each pixel thus measures a portion of the speckle pattern 20.

The data processing based on the measured light intensity of the individual pixels 4 will now be described making reference to FIG. 3.

Figure 3:
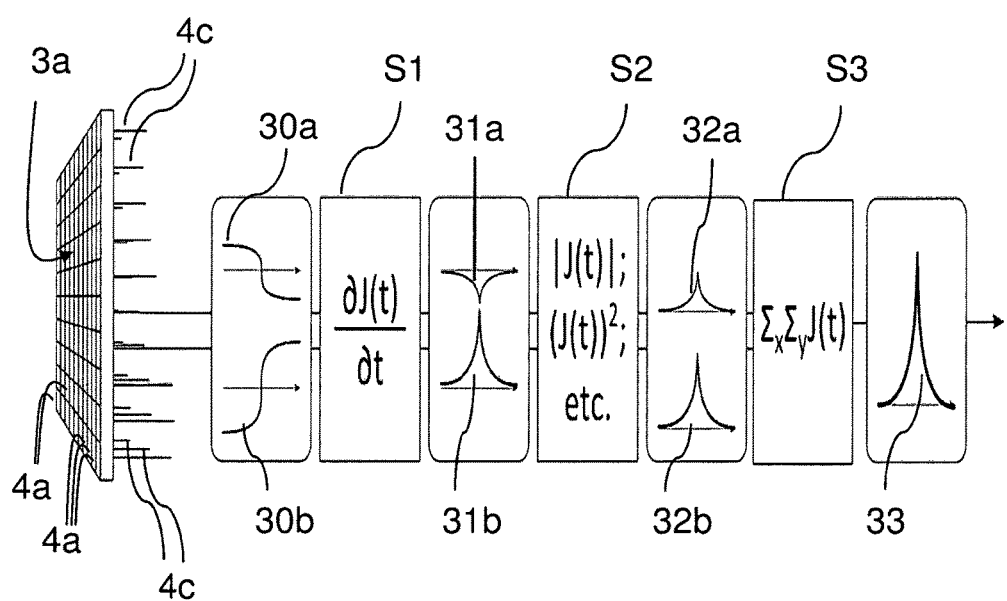
FIG. 3 shows a schematic illustration of the data processing of the detector according to an embodiment of the invention.

FIG. 3 shows a perspective view of the detection area 3a, which is subdivided into individual pixels 4a. Each pixel 4 outputs the variation over time of the light intensity on the respective pixel area (detection region) 4a in the form of a detection signal 4c. Labelled with the reference sign 30a, purely by way of example, such a temporal variation of a first pixel is measured, said pixel measuring a decrease in the light intensity as shown by the falling curve shape. At the same time, a second pixel can measure an increase in the light intensity, as denoted by the reference sign 30b.

Such a temporal change results from a movement within the sample or from a movement of a sample component, by which means the diffraction pattern 20 generated by the sample is changed.

In a first step S1, derivatives with respect to time are formed from the measured detection signals 4c of the individual pixels 4. The result of this differentiation operation is shown by way of example by the curves 31a and 31b. Subsequently, in step S2, the individual results, i.e. the differentiated measurement result of each pixel 4 is rectified, for example, by absolute value generation or squaring. The result of this rectification is shown, by way of example, by the curves 32a and 32b.

In a third step S3, the differentiated and rectified detection signals of all pixels 4 are summed (or alternatively averaged) and then provided as an output signal 6c of the detector 3. The result of this summation is shown, by way of example, by the curve 33.

In the present case, the differentiation with respect to time and subsequent rectification of the measurement data of the individual pixels is carried out by an integrated CMOS circuit 5 of the detector 3. This CMOS circuit thus outputs a differentiated and rectified signal 5c for each pixel. These output data of the CMOS circuit are subsequently summed in an adder 6.

The detector 3 thus appears outwardly as a detector which has only one data output 6c, via which a non-spatially resolved signal/data 7 is/are output. The signal that is non-spatially resolved in relation to the detector area 3a measures area-cumulatively, i.e. over the whole detection area, the total (or the average) of quantitative brightness changes that are generated by dynamic phenomena in the sample, at constant illumination intensity.

The movements in the sample then lead to the peaks in the output signal 7, which can easily be recognized.

Figure 4:
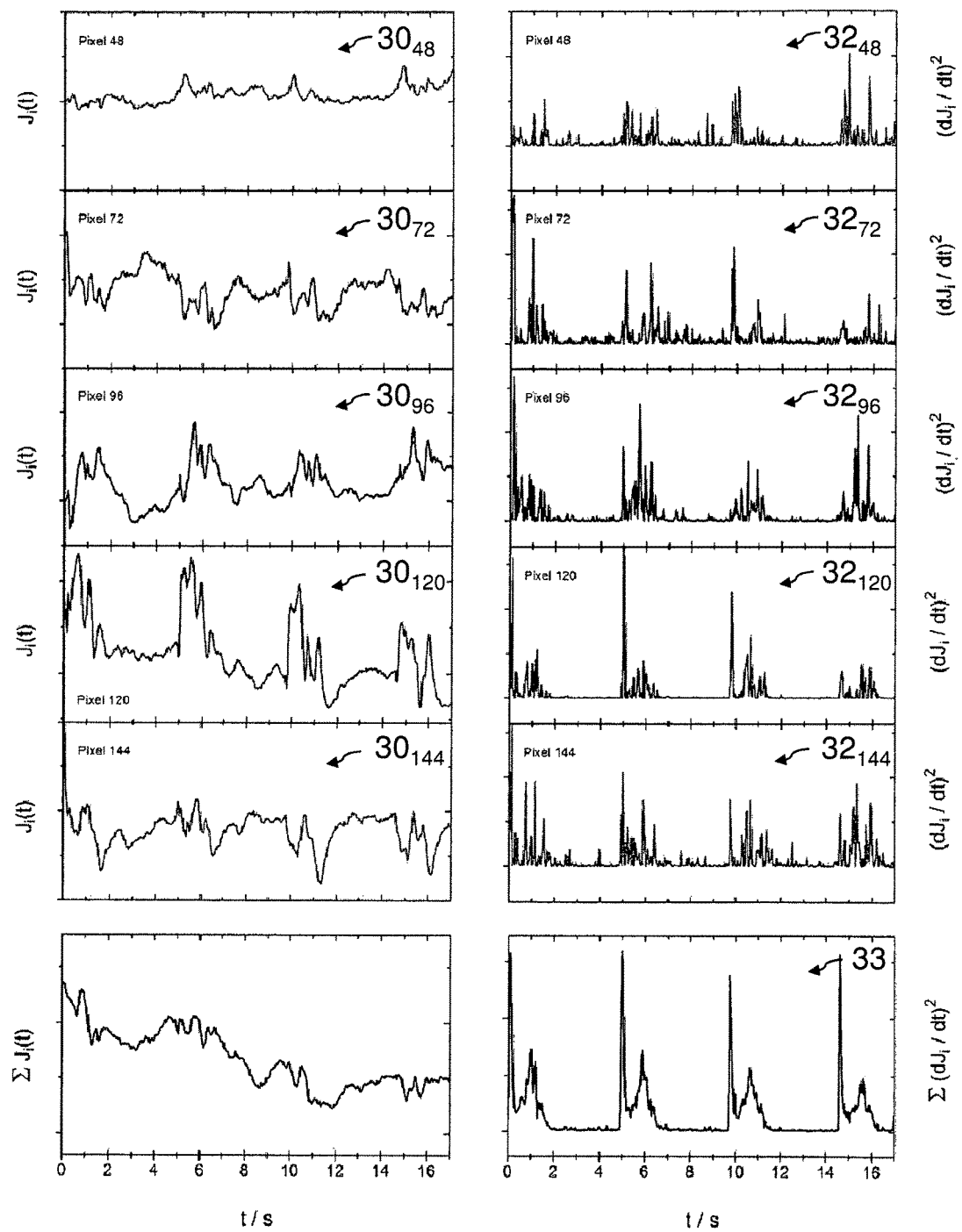
FIG. 4 shows the effect of the differentiation and rectification of the measurement values of individual pixels.

To clarify the advantages of the inventive approach, FIG. 4 illustrates the effect of the differentiation and rectification of the measurement values of randomly selected image areas (named "pixels" for simplification) 4 of the detection area 3a, in this case the pixels 48, 72, 96, 120, 144. Herein for demonstration of the method, the video of a speckle pattern recorded with a heart muscle tissue model was disassembled with video software into 192 image segments ("pixels") and the mean brightness of each segment recorded as a function of time ($J_i(t)$). With the aid of data analysis software, these $J_i(t)$ were differentiated and squared and subsequently, these processed data sets were summed ($\Sigma(\partial J_i/\partial t^2)$).

The five upper graphs in the left-hand column of FIG. 4 show the temporal variation 30 of the measured light intensity which is measured in each case by the pixels 48, 72, 96, 120, 144 of the detector 3. If the measurement values of all the image segments are summed, then the temporal variation shown in the bottom left-hand diagram of FIG. 4 results. A movement in the sample is not reliably detectable.

The five upper graphs in the right-hand column of FIG. 4 show the differentiated and subsequently rectified temporal variation 32 of the measured light intensity of the individual pixels 48, 72, 96, 120, 144.

If the processed values of all the image segments are summed, then the temporal variation 33 shown in the bottom right-hand diagram of FIG. 4 results. The movement in the sample is now readily detectable by means of the individual peaks of the variation 33.

Figure 5:
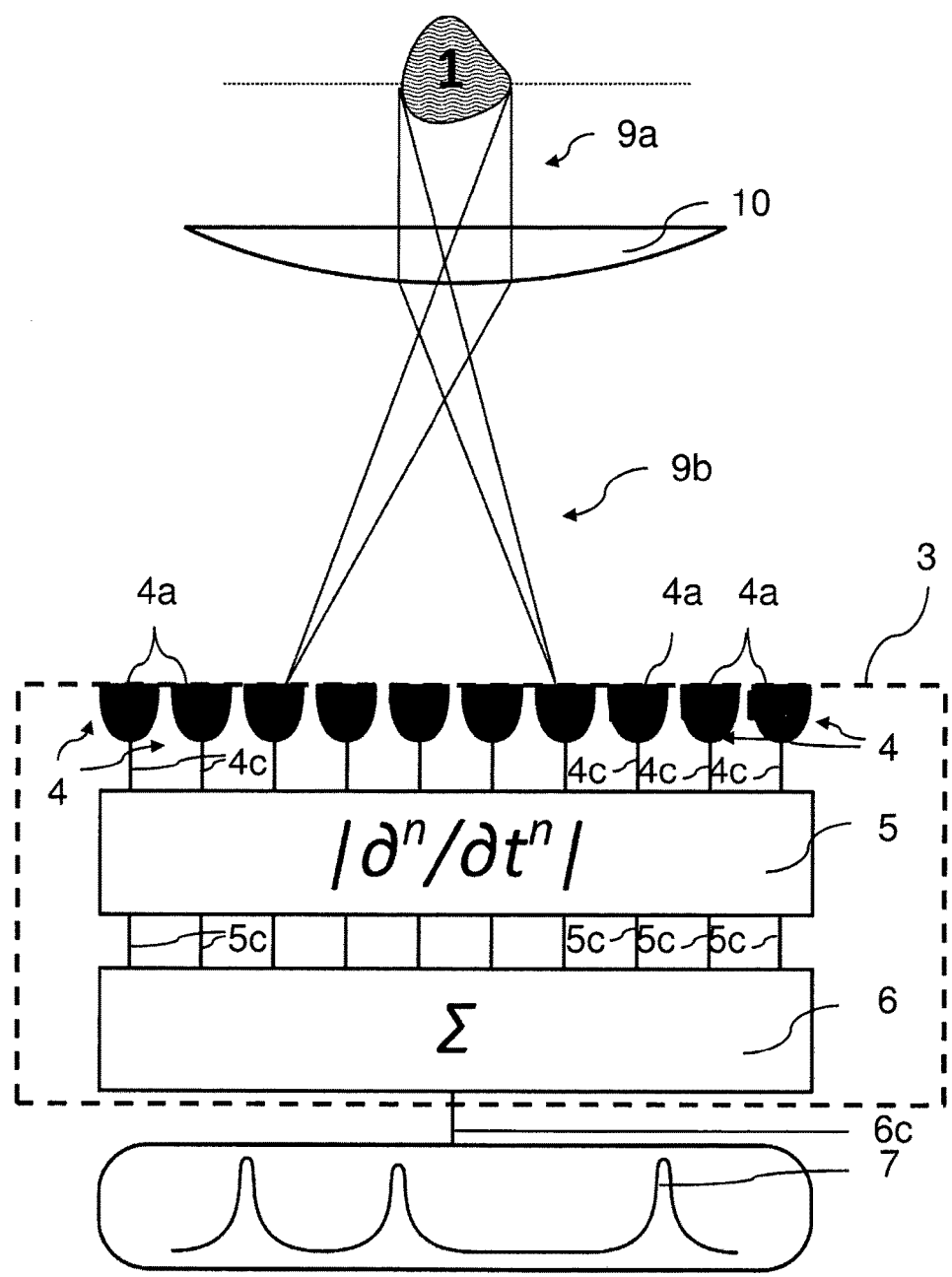
FIG. 5 shows a schematic representation of a method and a device according to a further embodiment of the invention.

FIG. 5 shows a schematic representation of a method and a device according to a further embodiment of the invention. Herein, components with the same reference signs correspond to the components of FIG. 1 and will not be described separately.

The whole biological sample 1 is illuminated by means of an optical wide-field illumination apparatus, i.e. without the use of an optical system for focusing on individual image planes within the sample or without the use of an optical system for successively scanning the sample volume. A peculiarity of this embodiment lies therein that the radiation source of the optical wide-field illumination apparatus does not generate coherent light. Consequently, no detectable diffraction pattern is generated by the sample 1. Rather, an optical system 10, for example in the form of a convex lens, of the optical wide-field illumination apparatus is provided by means of which an imaging ray path 9a, 9b is created in order to image the one focal plane of the sample 1 onto the detection area 3a of the detector 3. The optical wide-field illumination apparatus can be, for example, a transmitted-light microscope, a dark-field microscope or a wide-field fluorescence microscope. The processing of the measurement data takes place similarly to the exemplary embodiment described above. The embodiment with an imaging optical system is therefore also suitable for monitoring spatial samples, but the embodiment based on diffraction patterns is considered to be more advantageous.

Although the invention has been described making reference to particular exemplary embodiments, it is evident to a person skilled in the art that different amendments can be carried out and equivalents used as replacements without departing from the scope of the invention. In addition, many modifications can be made without departing from the associated scope. Consequently, the invention should not be restricted to the exemplary embodiments disclosed, but should encompass all exemplary embodiments that fall within the scope of the accompanying claims. In particular, the invention also claims protection for the subject matter and the features of the subclaims separately from the claims to which they refer.

The invention claimed is:

1. A method for a parallel optical in vitro detection of a respective movement: (i) in a plurality of mutually separate biological samples and/or (ii) of a sample component in the plurality of mutually separate biological samples, comprising the steps:
   a) providing
      a1) an optical wide-field illumination apparatus, which is configured to illuminate an entirety of each of the mutually separate biological samples, and
      a2) a receptacle for the mutually separate biological samples, which is a multiwell plate or a hanging drop multiwell plate having a plurality of cavities arranged in rows and columns to receive the mutually separate biological samples, and
      a3) a plurality of detectors in a form of a detector array for detecting radiation coming from the mutually separate biological samples, each detector of the plurality of detectors being assigned to a corresponding cavity of the plurality of cavities and having a detection area which is subdivided into a plurality of detection regions and is configured to form a derivative with respect to time of detection signals of individual detection regions, subsequently to rectify the detection signals, and to sum or to average differentiated and rectified detection signals of all the detection regions and then to provide them as an output signal;
   b) illuminating the mutually separate biological samples with the optical wide-field illumination apparatus; and
   c) detecting the respective movement dependent upon the output signal of a detector of the plurality of detectors.

2. The method according to claim 1, wherein the formation of the derivative with respect to time and the subsequent rectification of the detection signals of individual detection regions is carried out by an integrated circuit in each detector.

3. The method according to claim 1, wherein each detector outputs at least one of
   a single-channel signal and
   a signal or data that is not spatially resolved with respect to the detection area.

4. The method according to claim 1, wherein the optical wide-field illumination apparatus comprises a light beam source which generates coherent light wherein at least part of a diffraction pattern that is generated by the coherent light of the light beam source diffracted by a sample in a cavity of the receptacle is imaged on the detection area of the detector assigned to the cavity.

5. The method according to claim 1, wherein the optical wide-field illumination apparatus comprises a light beam source and an optical system, wherein the optical system is configured to generate an imaging ray path in order to image a sample in a cavity of the receptacle on the detection area of the detector assigned to the cavity.

6. The method according to claim 5, wherein the optical wide-field illumination apparatus is a transmitted-light microscope, a dark-field microscope or a wide-field fluorescence microscope.

7. The method according to claim 1, wherein at least one of a movement in a biological sample in a cavity of the receptacle and a movement of a component of the biological sample in the cavity of the receptacle is detected if at least one of a value of the output signal of the detector assigned to the cavity exceeds a pre-determined threshold value and the output signal has a periodicity.

8. The method according to claim 1, wherein the biological sample is at least one of a three-dimensional cell culture, three-dimensional tissue culture, three-dimensional cell cluster, and a sample of free-swimming microorganisms.

9. The method according to claim 1, wherein a diameter of the detection area of each detector is smaller than or equal to 9 mm.

10. The method according to claim 1, wherein a diameter of each biological sample is at least one of 50 micrometers in all spatial directions and greater than a refraction-limited resolution achievable by the optical wide-field illumination apparatus.

11. The method according to claim 1, wherein the formation of the derivative with respect to time and the subsequent rectification of the detection signals of individual detection regions is carried out by a CMOS circuit in each detector.

12. The method according to claim 1, wherein each detector is a non-image forming detector.

13. The method according to claim 1, wherein each biological sample comprises a plurality of cells.

14. A device for contact-free in vitro parallel optical detection of a respective movement: (i) in a plurality of mutually separate biological samples and/or (ii) of a sample component in the plurality of mutually separate biological samples, comprising:
  an optical wide-field illumination apparatus configured to illuminate an entirety of each of mutually separate biological samples, and
  a plurality of detectors in a form of a detector array for detecting optical radiation coming from the biological sample, each detector of the plurality of detectors having a detection area which is subdivided into a plurality of detection regions and is configured to form a derivative with respect to time of detection signals of individual detection regions, subsequently to rectify the detection signals, and to sum or to average the differentiated and rectified detection signals of all the detection regions and then to provide them as an output signal,
wherein:
a) the device is configured for the parallel optical detection of the respective movement,
b) the device is configured to receive a receptacle for the mutually separate biological samples which is a multiwell plate or a hanging drop multiwell plate having a plurality of cavities arranged in rows and columns to receive the mutually separate biological samples, and
c) each detector of the detector array is configured for assignment to a counterpart cavity of the plurality of cavities of the receptacle.

15. The device according to claim 14, wherein each detector has an integrated circuit which is configured to carry out formation of the derivative with respect to time and subsequent rectification of the detection signals of individual detection regions.

16. The device according to claim 14, wherein each detector outputs at least one of a single-channel signal, and a signal that is not spatially resolved with respect to the detection area.

17. The device according to claim 4, wherein each detector has a CMOS circuit which is configured to carry out the formation of the derivative with respect to time and the subsequent rectification of the detection signals of individual detection regions.

18. The device according to claim 14, wherein the detection area is subdivided into at least 100 or 10×10 multi-line adjacently arranged pixels.

19. An array of detectors wherein:
  a) each detector of the array of detectors is configured for detecting optical radiation with a detection area which is subdivided into a plurality of detection regions,
  b) each detector is configured to form a derivative with respect to time of detection signals of individual detection regions, subsequently to rectify the detection signals, and to sum or to average the differentiated and rectified detection signals of all the detection regions and then to provide them as an output signal,
  c) the array of detectors is configured for a parallel optical detection of a respective movement in a plurality of mutually separate biological samples or of a respective movement of a sample component in the plurality of mutually separate biological samples, and
  d) each detector is configured for assignment to a corresponding cavity of a multiwell plate or a hanging drop multiwell plate which has a plurality of cavities arranged in rows and columns to receive the plurality of mutually separate biological samples.

* * * * *